US012806028B2

(12) United States Patent
Wahab et al.

(10) Patent No.: US 12,806,028 B2
(45) Date of Patent: Nov. 24, 2026

(54) GLENOID IMPLANT FOR REVERSE SHOULDER PROSTHESIS

(71) Applicant: FX Shoulder Solutions, Viriat (FR)

(72) Inventors: Hassan Wahab, Angers (FR); Carlos Torrens, Castelldefels (FR); Herrick Siegel, Mountain Brook, AL (US); Umasuthan Srikumaran, Ellicott City, MD (US); Giorgio Gresta, Saint Just-Saint Rambert (FR)

(73) Assignee: FX Shoulder Solutions, Viriat (FR)

( * ) Notice: Subject to any disclaimer, the term of this patent is extended or adjusted under 35 U.S.C. 154(b) by 606 days.

(21) Appl. No.: 18/303,684

(22) Filed: Apr. 20, 2023

(65) Prior Publication Data

US 2023/0404767 A1 Dec. 21, 2023

(51) Int. Cl.
*A61F 2/40* (2006.01)
*A61F 2/30* (2006.01)

(52) U.S. Cl.
CPC .... *A61F 2/4081* (2013.01); *A61F 2002/4085* (2013.01)

(58) Field of Classification Search
None
See application file for complete search history.

(56) References Cited

U.S. PATENT DOCUMENTS 3,842,442 A 10/1974 Kolbel
8,118,875 B2 * 2/2012 Rollet .................. A61F 2/4014 623/19.12
8,241,366 B2 * 8/2012 Roche ...................... A61F 2/40 623/19.12
8,864,834 B2 * 10/2014 Boileau ............. A61B 17/1637 623/19.13
8,870,962 B2 * 10/2014 Roche ...................... A61F 2/40 623/19.12
11,771,561 B2 * 10/2023 Running ........... A61B 17/1778 623/19.13
12,011,357 B2 * 6/2024 Mehta ................ A61F 2/30771
2007/0156246 A1 * 7/2007 Meswania ................ A61F 2/40 623/19.12
2013/0150975 A1 * 6/2013 Iannotti ................ A61F 2/4059 623/19.11
2013/0261750 A1 * 10/2013 Lappin .............. A61B 17/8042 623/19.11
2014/0277518 A1 9/2014 Iannotti
2018/0193150 A1 * 7/2018 Winslow .................. A61F 2/30
2019/0175354 A1 * 6/2019 Knox ................... A61F 2/4003

FOREIGN PATENT DOCUMENTS

CN 104540475 A * 4/2015 ............... A61F 2/40
CN 111031968 A * 4/2020 .......... A61F 2/4081
FR 2776506 10/1999

(Continued)

*Primary Examiner* — Ann Hu
(74) *Attorney, Agent, or Firm* — Defillo & Associates, Inc.; Evelyn A. Defillo

(57) ABSTRACT

A glenoid implant for reverse shoulder prosthesis, having a base for anchoring the implant to a bone formed by a rod configured to extend through the thickness of the bone from a glenoid fossa, the rod including through-holes, and by screws for anchoring the rod configured to cross radially the rod, via the through-holes, and the bone, when the glenoid implant is implanted on the bone.

12 Claims, 5 Drawing Sheets

(56) References Cited

FOREIGN PATENT DOCUMENTS

| | | | | |
|---|---|---|---|---|
| FR | 3048357 | | 9/2017 | |
| WO | WO-2012051552 | A2 * | 4/2012 | ........... A61F 2/4059 |
| WO | WO2014075037 | | 5/2014 | |
| WO | WO-2014075037 | A1 * | 5/2014 | ......... A61B 17/1778 |
| WO | WO-2019133905 | A1 * | 7/2019 | ........... A61F 2/4612 |

* cited by examiner

GLENOID IMPLANT FOR REVERSE SHOULDER PROSTHESIS

FIELD OF THE INVENTION

The invention relates to a glenoid implant for reverse shoulder prosthesis, intended to be attached to the patient's glenoid fossa.

BACKGROUND OF THE INVENTION

A reverse total shoulder prosthesis comprises a humeral implant, in other words a part attached in the patient's humerus, and a glenoid implant, in other words a part attached on the patient's glenoid fossa (also called glenoid cavity). These two implants are hinged to each other to restore the mobility of the arm of the patient receiving surgery.

In case of a "reverse" total shoulder prosthesis, the center of rotation of the joint is shifted to the glenoid implant, unlike an "anatomic" prosthesis where it remains on the humeral implant.

This modification of the position of the center of rotation of the joint generates a modification of the muscles solicited to move the arm. In the present case, the deltoid muscle is solicited while, for an anatomic prosthesis, the rotator cuff muscles are solicited, i.e. the subscapularis, supraspinatus, infraspinatus and teres minor in addition to the deltoid. This modification of the muscles involved can be explained by irreparable damage of all or some of the rotator cuff muscles, such damage possibly occurring in old persons, in particular. In other words, and for persons suffering from irreparable damage to the rotator cuff muscles, a reverse shoulder prosthesis is preferred since it preserves the mobility of the shoulder from the first degrees of abduction of the arm with respect to the trunk. The reverse shoulder prosthesis therefore involves soliciting the deltoid muscle which is anchored to the humerus in a more distal manner than the rotator cuff muscles, thereby compensating for the damage to the rotator cuff muscles.

The reverse shoulder prosthesis is formed by a humeral implant comprising a hollow end (or cup) replacing the humeral head and, at the scapula, a bone anchoring base (or metaglene) to which a glenosphere that will collaborate with the cup positioned on the humerus is added.

Conventionally, the bone anchoring base present at the scapula is attached to this bone by several diverging anchor screws extending from the bone anchoring base. This spacing ensures that the glenoid implant is securely anchored by soliciting remote attachment points.

However, shoulder prostheses, and more particularly reverse shoulder prostheses, are used to restore the joint of persons suffering from osteoarthritis, in particular the reverse shoulder prosthesis for the reasons of shoulder mobility explained above. At an advanced stage of osteoarthritis, the damage to the joint, and more particularly to the glenoid cavity of the scapula, may be too serious to consider stable anchoring of the traditional glenoid implant. In other words, the available bone surface or bone capital is no longer sufficient (the bone wearing away), in particular at the portion connecting the glenoid cavity to the scapula, to guarantee stable anchoring of the bone anchoring base, which may jeopardize the possibility of restoring the joint with a shoulder prosthesis, even reverse.

SUMMARY OF THE INVENTION

The invention aims to provide a glenoid implant for reverse shoulder prosthesis allowing the use of a shoulder prosthesis for persons suffering from osteoarthritis at an advanced stage and for whom it would not be possible to consider the use of a prosthesis according to the prior art.

Thus, the invention relates to a glenoid implant for reverse shoulder prosthesis, comprising a base for anchoring the implant to a bone formed by a rod configured to extend through the thickness of the bone from a glenoid fossa, the rod comprising through-holes, and by screws for anchoring the rod configured to cross radially the rod, via the through-holes, and the bone, when the glenoid implant is implanted on the bone.

Thus, and instead of using an anchoring base that is difficult to stabilize, the rod extends through the thickness of the bone, in a bone trabecula, and is stabilized in the bone by anchor screws crossing radially the rod and the bone. Stable anchoring of the glenoid implant is therefore obtained, with a structure extending less (a rod) by using the bone areas that are less affected, which is particularly suitable for persons suffering from osteoarthritis at an advanced stage.

According to other optional characteristics of the glenoid implant taken alone or in combination:

- The glenoid implant comprises a glenosphere added to the rod;
- the rod comprises a surface for receiving a spacer for attaching the rod to the glenosphere;
- the receiving surface comprises a bore configured to collaborate with the spacer and a groove surrounding the bore, the groove being configured to interact with a tool for gripping and guiding the rod;
- the spacer is formed by a first portion for attaching the spacer to the rod and a second portion for attaching the spacer to the glenosphere, the first portion and the second portion being offset with respect to each other;
- the first portion and the second portion are inclined with respect to each other;
- the glenoid implant further comprises a part for stabilizing the glenoid implant with respect to the bone when the glenoid implant is implanted on the bone; and
- the stabilizing part comprises two stabilizing ends configured to extend each side of the bone when the glenoid implant is implanted on the bone.

The invention also relates to a reverse shoulder prosthesis comprising a glenoid implant according to the invention.

The invention also relates to a tool for gripping and guiding a glenoid implant according to the invention, comprising an end for locking to the rod and a gripping end, the gripping end extending at least partly parallel to the rod when the gripping and guiding tool is attached to the rod, the gripping end comprising at least one guiding hole to insert the anchor screws.

According to other optional characteristics of the glenoid implant taken alone or in combination:

- the gripping and guiding tool comprises at least one guiding element to insert the anchor screws that is removable with respect to the gripping end and which can extend between the guiding hole and a through-hole; and
- the gripping end is movable in rotation with respect to the locking end.

The invention also relates to a use of a glenoid implant according to the invention to form a joint prosthesis.

The invention also relates to a method for attaching a glenoid implant according to the invention to form a reverse shoulder prosthesis.

BRIEF DESCRIPTION OF THE FIGURES

The invention will be better understood on reading the following description, given solely by way of example and with reference to the accompanying drawings in which.

DETAILED DESCRIPTION

Figure 1:
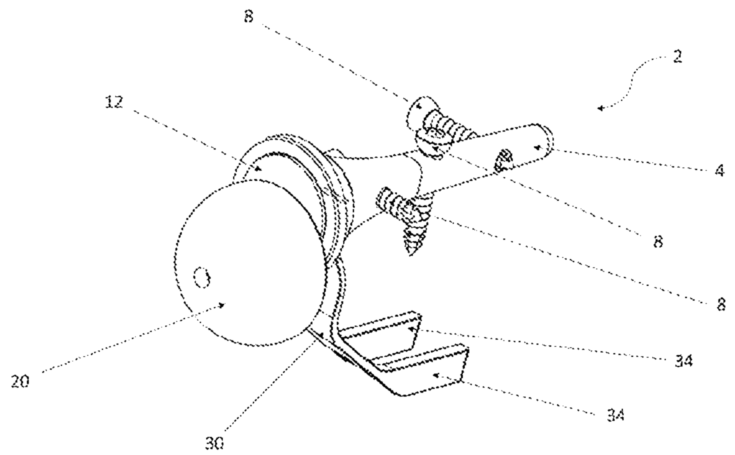
FIG. 1 is a perspective view of a glenoid implant for reverse shoulder prosthesis according to the invention.
Figure 2:
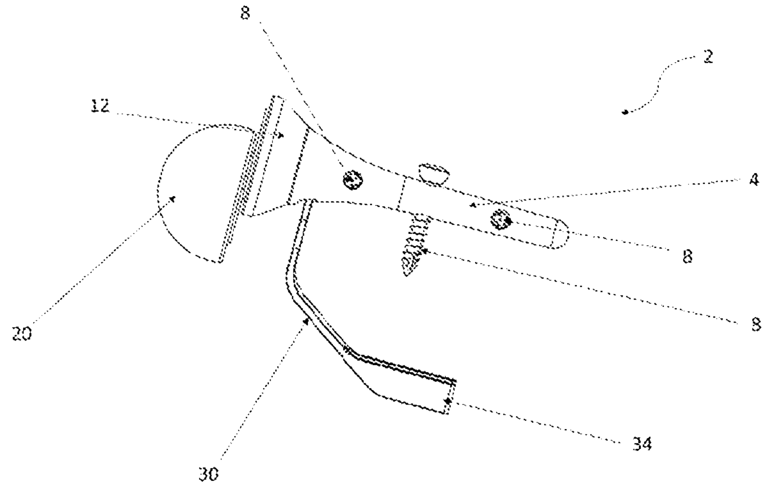
FIG. 2 is a side view of a glenoid implant for reverse shoulder prosthesis according to the invention.

We now refer to FIGS. 1 and 2 showing a glenoid implant 2 for reverse shoulder prosthesis.

Figure 3:
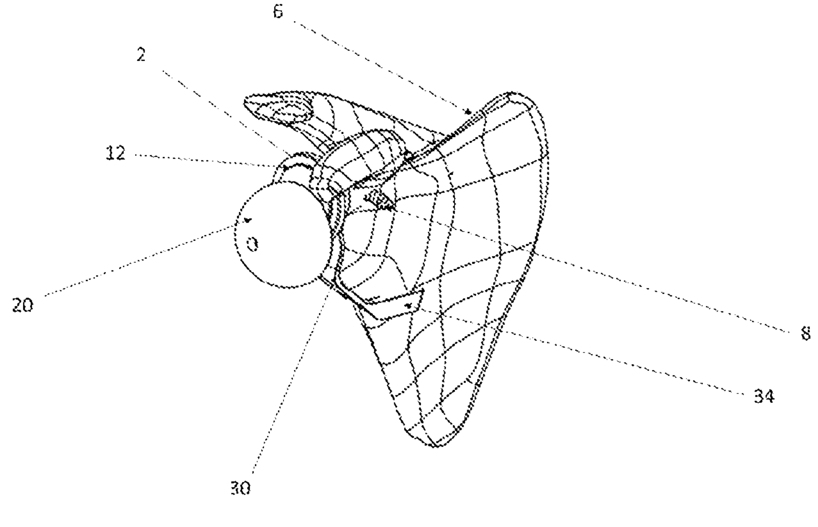
FIG. 3 is a perspective view of a glenoid implant for reverse shoulder prosthesis according to the invention placed on a scapula.

This glenoid implant 2 comprises an anchoring base formed by a rod 4 configured to extend through the thickness of a bone 6 (a scapula shown on FIG. 3) from a glenoid fossa and by screws 8 (or cortical screws) for anchoring the rod 4 in the bone configured to cross radially the rod 4 and the bone 6. As explained above, the rod 4 extends in a trabecula of the bone 6, for example at the junction between the scapula and the acromion, to allow anchoring, by inserting anchor screws 8, without extending too far into the bone 6, which could cause a problem in case of a severely advanced stage of osteoarthritis. We therefore understand that the surgeon will make a bore in the thickness of the bone 6 to house the rod 4 therein. The anchor screws 8 are then inserted to cross radially the bone 6 and the rod 4 (via through-holes 18 in the latter) and thus lock the rod 4 in the bone 6 as shown on FIG. 3. Obviously, it is understood that "radially" means in a direction perpendicular to a longitudinal axis A of the rod 4.

Figure 4:
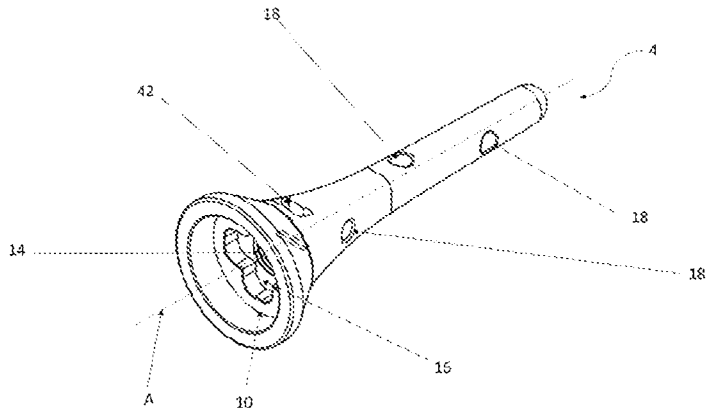
FIG. 4 is a perspective view of a rod of a glenoid implant for reverse shoulder prosthesis according to the invention.

The rod 4, shown alone on FIG. 4, is made of a biocompatible material having an optimum lifetime that is as long as possible. It may for example be made of a titanium alloy, stainless steel, cobalt chromium or a polymer material. The length of the rod 4 may vary to best adapt to the size of the bone 6, with a diameter of between 5 and 14 millimeters. It is therefore possible to design several rods 4 of variable sizes and variable length or a rod 4 formed by an assembly of several parts (each part may for example have at least one through-hole 18) of lengths that may vary in order to assemble a rod 4 adapted to the bone 6. For example, the length of the rod 4 may vary between 40 and 120 millimeters.

The rod 4 may comprise a face 10 for receiving a spacer 12, the receiving face 10 possibly comprising a bore 14, for example tapped, to attach the spacer 12 via a screw and/or a cone or a clip, for example by screwing if the bore 14 is tapped, possibly completed by a groove 16 forming a surface for interacting with a gripping and guiding tool 36 described below.

The rod 4 further comprises through-holes 18 for inserting the anchor screws 8, in this case three. Preferably, the through-holes 18 are made in areas of the rod 4 which will be located at the thickest areas of the bone 6. Thus, the anchor screws 8 will go through a thickness of bone 6 that is as large as possible. In addition, the rod 4 can be locked by soliciting the acromion and the coracoid.

As outlined above, the rod 4 can receive a spacer (or added ring) 12. The latter is used to form a remote link between the rod 4 and the glenosphere 20.

This spacer 12 may be formed in one piece or consist of several parts assembled to each other. It may be completely coaxial with the rod 4 or have an axis for attaching the glenosphere 20 that is offset with respect to the axis for attaching the spacer 12 to the rod 4. These attachment axes may or may not be parallel with each other. These various configurations can be used to adapt the glenoid implant 2 to the patient receiving it. The spacer 12 is added to the rod 4 once the latter has been locked to the bone 6.

Figure 5:
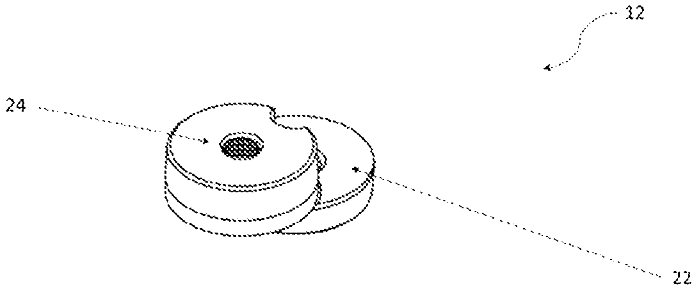
FIG. 5 is a perspective view of a first variant of a spacer of a glenoid implant for reverse shoulder prosthesis according to the invention.
Figure 6:
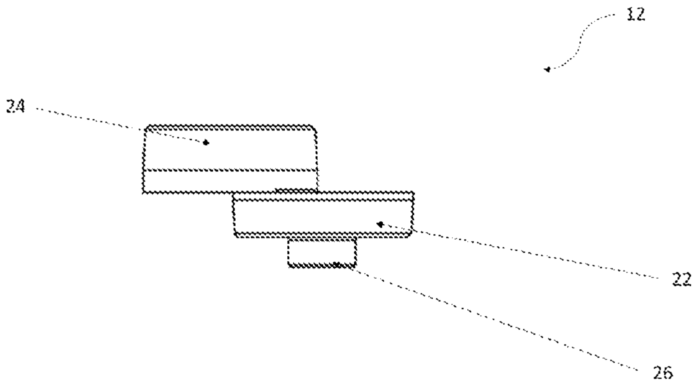
FIG. 6 is a side view of a second variant of a spacer of a glenoid implant for reverse shoulder prosthesis according to the invention.

FIGS. 5 and 6 show a first variant of a spacer 12. The latter is formed of two portions 22 and 24 made in one piece but offset, for example by 1 to 25 millimeters from each other. The first portion 22, used to connect the rod 4 to the spacer 12, comprises a first hole used to make this link, for example by screwing if it is threaded and/or tapered. This hole is aligned with the bore 14 of the rod 4. The second portion 24, used to connect the glenosphere 20 to the spacer 12, comprises a second hole used to make this link, for example by screwing if it is tapped and by collaborating with a protrusion 28 of the glenosphere 20 comprising an external thread. A Morse cone can also be used to make the attachment. The portions are parallel to each other.

Figure 7:
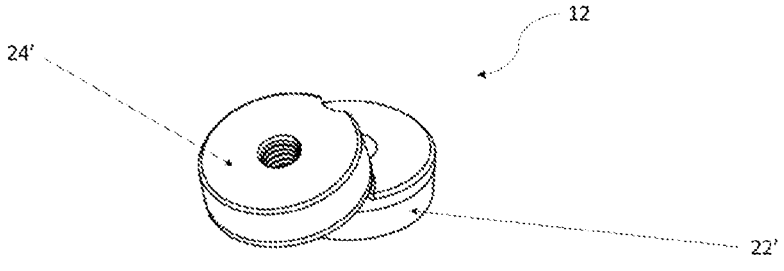
FIG. 7 is a perspective view of a second variant of a spacer of a glenoid implant for reverse shoulder prosthesis according to the invention.
Figure 8:
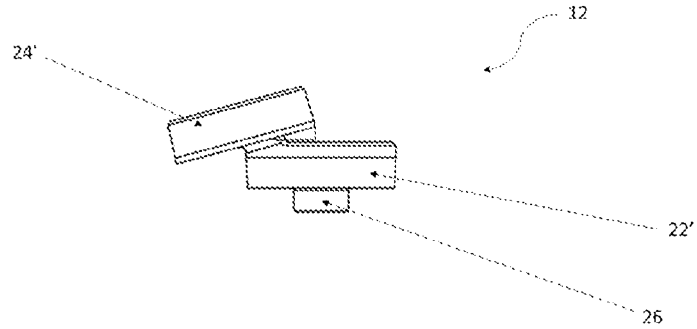
FIG. 8 is a side view of a second variant of a spacer of a glenoid implant for reverse shoulder prosthesis according to the invention.

FIGS. 7 and 8 show a second variant of a spacer 12. The latter is formed of two portions 22' and 24' made in one piece but offset, for example by 1 to 25 millimeters from each other. The first portion 22', used to connect the rod 4 to the spacer 12, comprises a first hole used to make this link, for example by screwing if it is threaded. This hole is aligned with the bore 14 of the rod 4. The latter has a protuberance 26 that collaborates with the groove 16 as explained above. The second portion 24', used to connect the glenosphere 20 to the spacer 12, comprises a second hole used to make this link, for example by screwing if it is threaded and by collaborating with a protrusion 28 of the glenosphere 20 comprising an external thread. The portions are inclined with respect to each other, for example by forming an angle of between 5° and 30°, so that the glenosphere 20 can be attached inclined with respect to the rod 4.

As for the rod 4, the spacer 12 is made of a biocompatible material having an optimum lifetime that is as long as possible, allowing good distribution of the mechanical stresses. The spacer 12 can in particular be made entirely or partially of metal, plastic or ceramic. It can also be made of several different materials, including a composition of the above-mentioned materials.

In the examples described, the spacer 12 is a part added to the rod 4. It could also be made in one piece with the latter and form an end of the rod 4.

Figure 10:
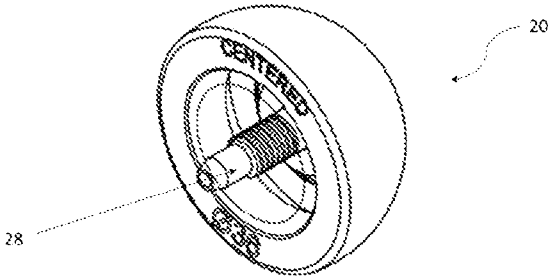
FIG. 10 is a perspective view of a first variant of a glenosphere of a glenoid implant for reverse shoulder prosthesis according to the invention.
Figure 11:
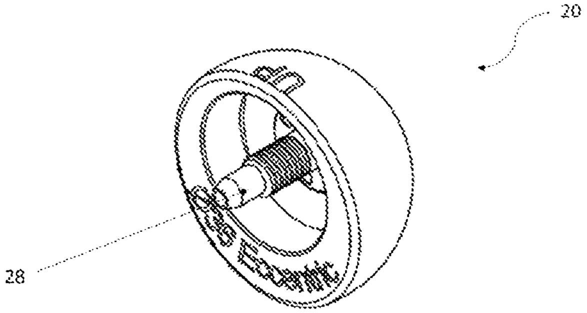
FIG. 11 is a perspective view of a second variant of a glenosphere of a glenoid implant for reverse shoulder prosthesis according to the invention.

The glenosphere 20 is shown on FIGS. 10 and 11. This glenosphere 20 can be spherical (half-sphere, portion of sphere greater than a half-sphere, portion of sphere extended with a cylindrical portion). Its diameter may be between 30 and 46 millimeters. Obviously, this diameter may be outside this range. It can be made of ceramic. Any type of ceramic known by those skilled in the art can be used. For example, it could be alumina, zirconia or a composite material. Since ceramic is a hard material, it can be used with pairs of "hard/hard" or "hard/soft" materials. In this second example, the "soft" material can be ultra-high-molecular-weight polyethylene (UHMWPE) or polyetheretherketone (PEEK) or polyetherketoneketone (PEKK) or their derivatives.

The glenosphere 20 can be centered or not and can be lateralized if necessary (as described above, in particular depending on the shape of the spacer 12). Centering means that a protrusion 28 that is used to attach the glenosphere 20 to the spacer 12 extends from the center of the flat surface of the hemisphere in a direction perpendicular to the plane in which the flat surface of the hemisphere extends. Off-centering, for example between 1 and 4 millimeters, means that a protrusion 28 that is used to attach the glenosphere 20 to the spacer 12 does not extend from the center of the flat surface of the hemisphere. The protrusion 28 may comprise an external thread in order to screw the glenosphere 20 onto the spacer 12, more particularly in the hole of the second portion 24 or 24' of the spacer 12, threaded in this case as described above.

The glenosphere 20 can be marked, for example by engraving, to indicate its diameter, the fact that it is centered or off-centered or, and if necessary, to write text identifying the portion of the glenosphere 20 to be placed at an angle towards the upper position of the scapula, in other words "UP" in the example shown on FIG. 11 of the off-centered glenosphere.

The possibility of using a glenosphere 20 of variable diameter, centered of off-centered, provides an additional possibility for adapting the glenoid implant 2 to the patient, in addition to the choice of the shape of the spacer 12 and the size of the rod 4.

Figure 9:
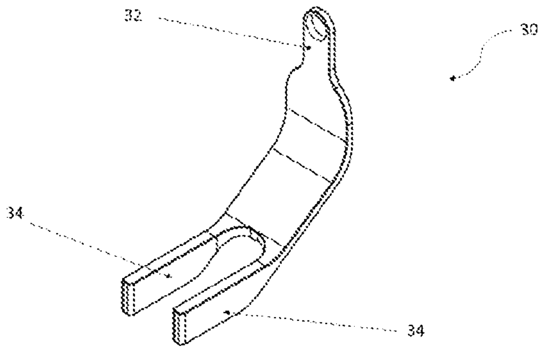
FIG. 9 is a perspective view of a part for stabilizing a glenoid implant for reverse shoulder prosthesis according to the invention.

The glenoid implant 2 may further comprise a stabilizing part 30 (or stabilizing fork). The latter, shown alone on FIG. 9 or fitted on the rod 4 on FIGS. 1 to 3, can be added to the rod 4, which therefore comprises a slot 42 for attaching the stabilizing part 30. More precisely, the attachment slot 42 may open out at an internal tapping of the rod 4. An intermediate part comprising an external thread may therefore be screwed onto the rod 4 and lock the stabilizing part 30.

This stabilizing part 30 may comprise an end 32, advantageously drilled, for locking the stabilizing part 30 to the rod 4 and two stabilizing ends 34. The latter are arranged opposite each other so as to extend each side of the bone 6 (in this case the scapula) when the glenoid implant 2 is positioned. At least one stabilizing end 34 could rest against the bone 6 when the glenoid implant 2 is positioned. In this case, it can have a flat surface extending parallel to the bone 6 in order to rest against a large area. The number and shape of the stabilizing ends 34 may vary.

The stabilizing part 30 could also provide additional bone anchoring for the glenoid implant 2. At least one stabilizing end 34 (or the stabilizing end if there is only one) may in this case comprise a through-hole to attach it to the bone 6, for example by screwing, and thus create an additional anchor point.

As described above for other elements, the stabilizing part 30 is made of a biocompatible material having an optimum lifetime that is as long as possible, allowing good distribution of the forces. It may for example be made of a titanium alloy, stainless steel, cobalt chromium or a polymer material.

Figure 12:
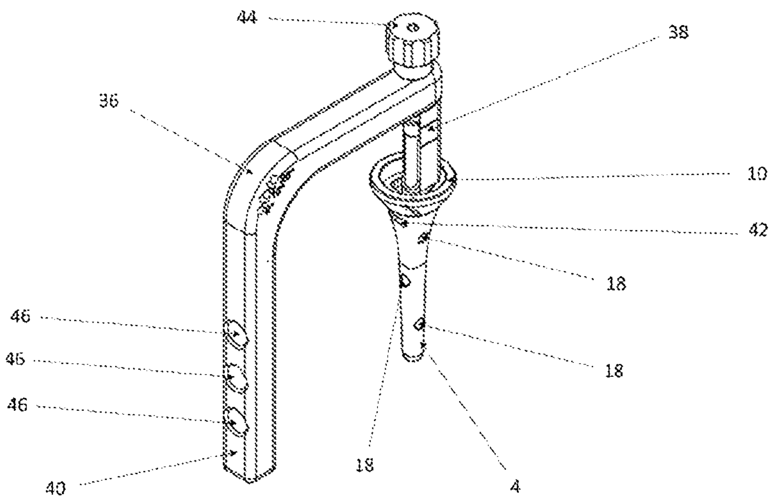
FIG. 12 is a perspective view of a rod of a glenoid implant for reverse shoulder prosthesis according to the invention, attached to a tool for gripping and guiding the rod.

FIG. 12 shows the rod 4 attached to a gripping and guiding tool 36. The latter comprises a locking end 38 configured to collaborate with the groove 16 and the bore 14 in order to attach the rod 4 to the gripping and guiding tool 36 and place the rod in the cavity formed in the bone 6. The gripping and guiding tool 36 also comprises an end 40 allowing a surgeon to grip the assembly formed by the tool and the rod 4.

Figure 13:
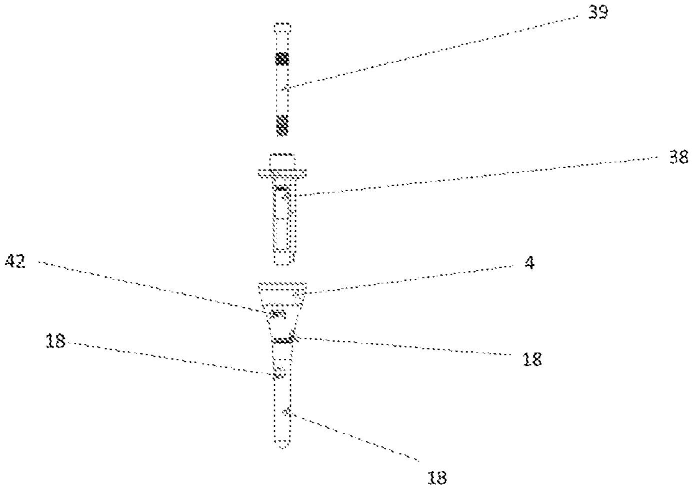
FIG. 13 is an exploded view of a rod of a glenoid implant for reverse shoulder prosthesis according to the invention, and a part of a tool for gripping and guiding the rod.

The locking end 38 and the gripping end 40 are advantageously two separate parts of the gripping and guiding tool 36. Consequently, the locking end 38 is firstly added to the rod 4 (whether or not the latter is provided with the stabilizing part 30). This locking end 38 is advantageously hollow and partially tapped in order to insert an intermediate part 39 comprising at least an external thread in order to lock by screwing the locking end 38 onto the rod 4 (see FIG. 13).

Figure 14:
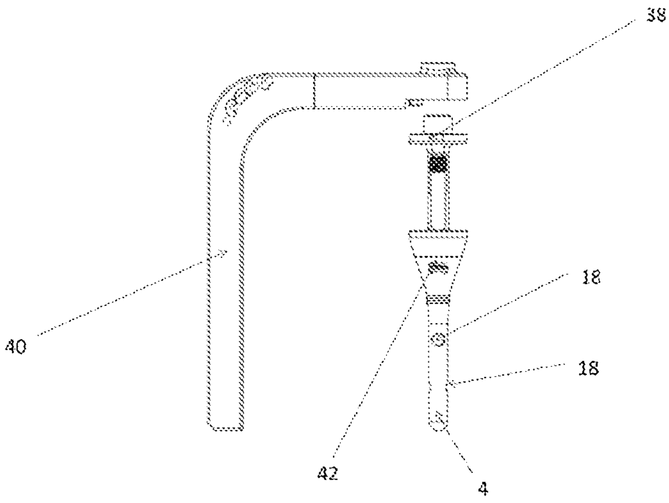
FIG. 14 is a perspective view of a rod of a glenoid implant for reverse shoulder prosthesis according to the invention, being connected to a tool for gripping and guiding the rod.
Figure 15:
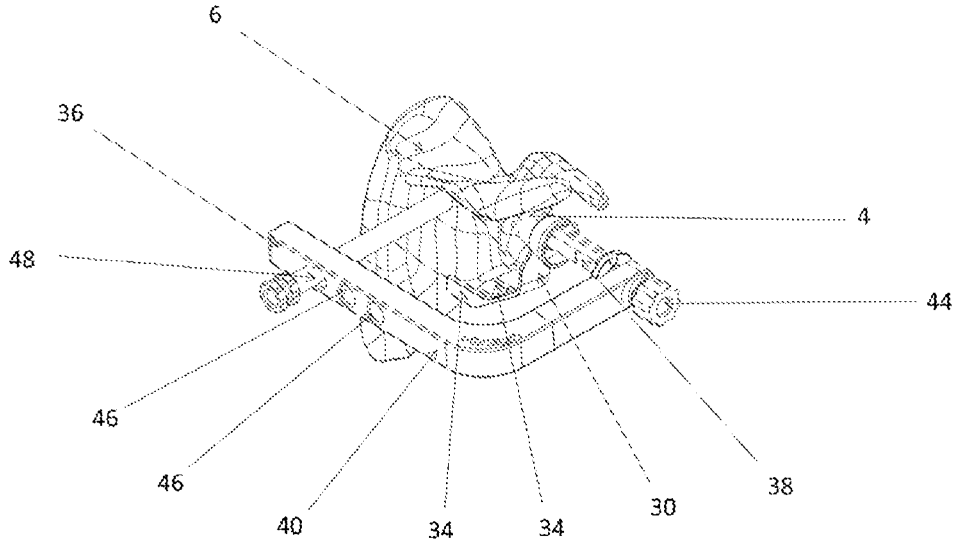
FIG. 15 is a perspective view of a glenoid implant being implanted on a scapula.

The gripping end 40 is then added to the locking end 38 (see FIG. 14) and attached to the latter, for example by screwing them to each other, for example by a knurled head screw 44 shown on FIGS. 12 and 15.

The gripping end 40 comprises a part extending parallel to the rod 4 when the latter is held by the gripping and guiding tool 36 and comprises holes 46 that can be aligned with the through-holes 18. These guiding holes 46 are used to guide a surgeon when positioning the rod 4. The alignment allows the surgeon to know where to drill the bone 6 to reach a through-hole 18. To do this, the surgeon can position a guiding element 48, in this case of cylindrical shape, that extends from the guiding holes 46 and perpendicularly to the rod 4 and to the part of the gripping end 40 that has the guiding holes 46 (see FIG. 15). This guiding element 48 then abuts against the bone 6 and is advantageously hollow in order to insert therein means for drilling the bone 6 then the anchor screws 8 and means for screwing the latter to the rod 4. The anchor screws 8 then cross through the bone 6 and the rod 4.

FIG. 15 shows a rod 4, that has a stabilizing part 30, already inserted in a cavity formed in the thickness of the bone 6. The gripping end 40 is positioned so as to align at least one guiding hole 46 with a through-hole 18 (not shown on this Figure). A guiding element 48 extends from a hole 46 and is pressed against the bone 6.

As shown on FIG. 4, the through-holes 18 may not be aligned and at least two of them may extend in different directions. In this case, it is advantageous to allow the gripping end 40 to rotate with respect to the locking end 38. Thus, the gripping end 40 can be moved to align a guiding hole 46 with a through-hole 18. On FIG. 4, two through-holes 18 are aligned and the third is shifted by 90°. The gripping end 40 can therefore pivot through 90° to align with one of the through-holes 18.

LIST OF REFERENCES

2: glenoid implant
4: rod
6: bone
8: anchor screw
10: receiving surface
12: spacer
14: bore
16: groove
18: through-holes
20: glenosphere
22, 22': first portions of the spacer
24, 24': second portions of the spacer
26: protuberance
28: protrusion
30: stabilizing part
32: locking end
34: stabilizing end
36: gripping and guiding tool
38: locking end
39: intermediate part
40: gripping end
42: attachment slot
44: knurled head screw
46: guiding holes
48: guiding element
A: longitudinal axis of the rod

What is claimed is:

1. A glenoid implant for reverse shoulder prosthesis comprising a base for anchoring the implant to a bone formed by a rod configured to extend through a thickness of the bone from a glenoid fossa, the rod comprising through-holes, and being anchored in the bone by screws configured to cross radially the rod, via the through-holes, and the bone, when the glenoid implant is implanted on the bone, wherein the rod is formed of a plurality of parts movable relative to one another so as to form a rod of variable length, between 40 and 120 mm.

2. The glenoid implant according to claim 1, further comprising a glenosphere added to the rod.

3. The glenoid implant according to claim 2, wherein the rod comprises a surface for receiving a spacer for attaching the rod to the glenosphere.

4. The glenoid implant according to claim 3, wherein the receiving surface comprises a bore configured to collaborate with the spacer and a groove surrounding the bore, the groove being configured to interact with a tool for gripping and guiding the rod.

5. The glenoid implant according to claim 3, wherein the spacer is formed by a first portion for attaching the spacer to the rod and a second portion for attaching the spacer to the glenosphere, the first portion and the second portion being offset with respect to each other.

6. The glenoid implant according to claim 5, wherein the first portion and the second portion are inclined with respect to each other.

7. The glenoid implant according to claim 1, further comprising a part for stabilizing the glenoid implant with respect to the bone when the glenoid implant is implanted on the bone.

8. The glenoid implant according to claim 7, wherein the stabilizing part comprises two stabilizing ends configured to extend on either side of the bone when the glenoid implant is implanted on the bone.

9. A reverse shoulder prosthesis comprising a glenoid implant according to claim 1.

10. A tool for gripping and guiding a glenoid implant according to claim 1, comprising an end for locking to the rod and a gripping end, the gripping end extending at least partly parallel to the rod when the gripping and guiding tool is attached to the rod, the gripping end comprising at least one guiding hole to insert the anchor screws.

11. The gripping and guiding tool according to claim 10, comprising at least one guiding element to insert the anchor screws that is removable with respect to the gripping end and which can extend between the guiding hole and a through-hole.

12. The gripping and guiding tool according to claim 10, wherein the gripping end is movable in rotation with respect to the locking end.

* * * * *